(12) United States Patent
Jahn et al.

(10) Patent No.: US 6,542,761 B1
(45) Date of Patent: Apr. 1, 2003

(54) MULTIFUNCTION SENSOR

(75) Inventors: Paul Jahn, Frankfurt (DE); Franz Wilhelm Koerdt, Bad Nauheim (DE); Matthias Krämer, Friedrichsdorf (DE); Klaus Metzner, Friedrichsdorf (DE); Harald Peter, Oberursel (DE); Walter Pieper, Florstadt (DE); Bernd Steinbach, Friedberg (DE)

(73) Assignee: Fresenius Medical Care Deutschland GmbH, Bad Homburg (DE)

( * ) Notice: Subject to any disclaimer, the term of this patent is extended or adjusted under 35 U.S.C. 154(b) by 0 days.

(21) Appl. No.: 09/377,287

(22) Filed: Aug. 19, 1999

(30) Foreign Application Priority Data

Aug. 19, 1998 (DE) ......................... 198 37 667

(51) Int. Cl.[7] .............................. A61B 5/00
(52) U.S. Cl. ............... 600/310; 600/368; 600/476; 604/27
(58) Field of Search .............. 604/3–7, 403–416, 604/27–29; 600/309–311, 316, 322–327, 332, 364–366, 372–375, 377–382; 210/321.6–321.68, 634, 641–646

(56) References Cited

U.S. PATENT DOCUMENTS

| 4,072,056 A | 2/1978 | Lee | |
|---|---|---|---|
| 4,923,444 A | * 5/1990 | Daoud et al. | 604/131 |
| 4,972,844 A | * 11/1990 | Cianci et al. | 600/573 |
| 5,195,976 A | * 3/1993 | Swenson | 604/113 |
| 5,385,539 A | * 1/1995 | Maynard | 604/6.08 |
| 5,560,362 A | * 10/1996 | Sliwa, Jr. et al. | 600/439 |
| 5,563,347 A | 10/1996 | Martin et al. | |
| 6,139,523 A | * 11/2000 | Taylor et al. | 604/98.01 |

FOREIGN PATENT DOCUMENTS

| DE | 29 30869 | 10/1986 |
| DE | 38 27553 C1 | 10/1989 |
| DE | 44 19 593 A1 | 12/1995 |
| EP | 0 130 441 b1 | 1/1985 |
| EP | 0 374 858 | 6/1990 |
| EP | 0 392 897 A2 | 10/1990 |

* cited by examiner

Primary Examiner—Eric F. Winakur
Assistant Examiner—Matthew Kremer
(74) Attorney, Agent, or Firm—Kenyon & Kenyon

(57) ABSTRACT

A device for measuring parameters of medical fluids having a measurement chamber through which the fluid to be measured passes. The chamber is sealed on one side by a flexible membrane, and it also has a measurement plate that has a peripheral seal on its outer edge and is in contact with the flexible membrane. At least one sensor for measuring a parameter of the medical fluid is mounted on the measurement plate, and the measurement plate has a continuous inlet leading to the flexible membrane so that a vacuum can be established between the measurement plate and the flexible membrane.

18 Claims, 1 Drawing Sheet

MULTIFUNCTION SENSOR

The present invention relates to a device for measuring the parameters of fluids treated during medical procedures. More specifically, the invention relates to a system for air detection as well as pressure monitoring in the arterial and venous blood treated in an extracorporeal cycle during dialysis treatment. In addition, measurement of the blood volume and blood temperature are also carried out by the invention.

DESCRIPTION OF RELATED ART

German Patent No. 38 27 553 C1 describes a device for measuring the change in the intravascular blood volume during blood filtration in a blood purification device. At least one ultrasonic sensor is provided in the extracorporeal blood cycle, and is connected to an analyzer unit. At the start of filtration, a first ultrasonic signal is recorded and the change in ultrasonic signals is determined during filtration. The change in hematocrit is determined from the change in ultrasonic signals, permitting a determination of the change in intravascular blood volume. The measurement is based on the relationship between the velocity of sound in the blood and the protein content in the blood.

German Patent No. 44 19 593 A1 describes a device for noninvasive measurement of the pressure of a medium. This device is constituted of a pressure measurement chamber through which blood, for example, is passed. The pressure measurement chamber has a passage which is sealed by a membrane. Beneath the membrane is a rubber ring against which a pressure sensor is pressed, so that both positive and negative pressures can be measured.

European Patent No. 0 392 897 A2 describes a glass fiber sensor with which pressure, temperature and flow rate can be measured. The glass fiber is terminated at one end with reflective and temperature-dependent materials. The quantity of light reflected in the fiber is proportional to the pressure against the terminated element.

European Patent No. 0 130 441 B1 describes a pressure measurement device, where contact between a pressure chamber and a pressure sensor is ensured by suction applied to the pressure chamber against the pressure sensor. The pressure sensor thus can measure the pressure changes in the pressure chamber.

During a dialysis treatment, it is necessary to measure all the above-mentioned parameters. Conventionally, several of these measurement devices must thus be provided, requiring specialized connections between the measuring machines and the extra corporeal blood cycle. This results in a considerable expense to obtain the measurements.

SUMMARY OF THE INVENTION

The present invention is directed to a sensor device capable of measuring all the parameters necessary for monitoring treatment of medical fluids using a single, common measurement head, that substantially obviates one or more of the problems due to the limitations and disadvantages of the related art. Additional features and advantages of the invention will be set forth in the description which follows, and in part will be apparent from the description, or may be learned by practice of the invention. Other advantages of the invention will be realized and obtained by the apparatus and method particularly pointed out in the written description and claims hereof, as well as the appended drawings.

To achieve these and other advantages and in accordance with the purpose of the invention, as embodied and broadly described, the invention is a device for measuring selected parameters of medical fluids that includes a measurement chamber through which the fluid flows, sealed on at least one side by a flexible membrane, a measurement plate having a peripheral seal on an outer edge, in contact with the flexible membrane, at least one sensor for measuring the selected parameters of the medical fluid disposed on the measurement plate, and a continuous inlet formed in the measurement plate leading to the flexible membrane, so that a vacuum can be established between the measurement plate and the flexible membrane.

According to the present invention, the device includes a measurement chamber through which passes the fluid on which the measurement is to be performed. The measurement chamber is sealed with a flexible membrane on one wall, and a measurement plate which has a peripheral seal on its outer edge is in contact with the flexible membrane. At least one sensor for measuring a parameter of the medical fluid is mounted on the measurement plate. The measurement plate has a continuous inlet leading to the flexible membrane, through which a partial vacuum can be established between the measurement plate and the flexible membrane.

Several sensors can be mounted on the measurement plate, and since the flexible membrane can be brought in close contact with the measurement plate, the medical fluids are separated from the sensors on the measurement plate only by the flexible membrane. Because of the peripheral seal disposed on the measurement plate, the flexible membrane can be brought in close contact with the underside of the measurement plate by applying a vacuum, so that very close contact can be established between the sensors and the specimen of medical fluid in the measurement chamber. The contact surface of at least one sensor is preferably flush with the underside of the measurement plate, so that it is possible to establish direct measurement contact between the respective sensor and the flexible membrane.

Because of advances in miniaturization and integration technology of sensors, it is possible to arrange multiple sensors on an area a few square centimeters in size. Each respective sensor is preferably mounted in a recess in the measurement plate, with the measurement surface of the sensor being in flush contact with the underside of the measurement plate. The sensors are preferably securely glued to the measurement plate.

In particular, a pressure sensor and a temperature sensor may be used in the invention. Pressure sensors have become available formed on individual semiconductor chips due to advances in integration of Microsystems, so that the chips carrying the sensor are only a few square millimeters in size. Because the sensor surface can be brought in direct contact with the membrane, it is possible to measure both positive and negative pressures. As a result, the thermal energy balance and the venous pressure in a dialysis machine can be measured with the pressure sensor and the temperature sensor according to the invention.

According to another embodiment of the present invention, another measurement plate with a peripheral seal on its edge is provided, and is kept at a selected distance from and substantially parallel to the first measurement plate by means of spacers. The measurement chamber is then inserted between the two measurement plates. One side of the measurement chamber is formed by a second flexible membrane forming a seal with the additional measurement plate. Each measurement plate has a continuous inlet leading to the respective flexible membrane, so that a vacuum can be created between each of the measurement plates and the flexible membranes.

Because of the use of parallel measurement plates, an ultrasonic propagation time measurement can be performed, with an ultrasonic sensor being mounted on one of the measurement plates for this purpose. An ultrasonic pulse is emitted by the ultrasonic sensor, is reflected by the opposite plate, and then is received back by the ultrasonic sensor. The spacers guarantee that there is no change in the distance between the two measurement plates, so that very accurate ultrasonic propagation time measurements can be performed.

The parallel measurement plates can also be used to perform transit measurements on the specimen. To do so, at least one transmitting element is mounted on one measurement plate, and at least one receiver element paired with the transmitting element is mounted on the other measurement plate. The transmitting element may include, for example, an ultrasonic transmitter, a light source, or other transmission device. The receiver element can include a corresponding ultrasonic receiver, a light receiver, or other receiving device mounted on the opposite plate.

According to one exemplary embodiment, the ultrasonic measurement method can be carried out using opposite ultrasonic sensors to determine the relative blood volume of the fluid in the measurement chamber. The device according to the present invention also makes it possible to avoid the use of an expensive measurement chamber, such as one made of glass, that is used in conventional devices to ensure a constant distance between ultrasonic elements. Instead, a constant distance between the measurement plates is ensured by spacers.

In addition, with the present invention it is also possible to detect air bubbles in the fluid specimen being measured, using opposing ultrasonic sensors.

An optical detector formed of a light source and a light receiver may also be used, for example in the automatic detection of the presence of blood, or for detection of air bubbles.

In one preferred embodiment, the seal of the measurement plate is made of a rubber ring which is inserted into a groove in the measurement plate and projects slightly above the edge of the measurement plate. As soon as a vacuum is established between the membrane and the measurement plate, the membrane is pressed tightly against the underside of the measurement plate by the ambient air pressure, and the seal guarantees that no additional air can flow into the area between the measurement plate and the flexible membrane.

The flexible membrane can be made, for example, of a thin plastic film, while the measurement chamber may be made of a plastic chamber with rigid walls. It is especially advantageous if the flexible membrane and the measurement chamber are integrated into a disposable plastic part. Centering holes may be provided in the disposable part so that the spacers engage in them and thus reliably and securely position the disposable part with respect to the measurement plates.

The respective measurement plates are preferably made of a metal disk into which the respective sensors are inserted. In a preferred embodiment, the metal disk is kept at a constant temperature by, for example, Peltier elements. This design permits a more accurate temperature measurement of the respective specimen.

It is to be understood that both the foregoing general description and the following detailed description are exemplary and explanatory and are intended to provide further explanation of the invention as claimed.

BRIEF DESCRIPTION OF THE DRAWINGS

The accompanying drawing is included to provide a further understanding of the invention and is incorporated in an constitutes part of this specification, illustrates several embodiments of the invention and together with the description serves to explain the present invention. In the drawings:

DETAILED DESCRIPTION OF THE EMBODIMENTS

Figure 1:
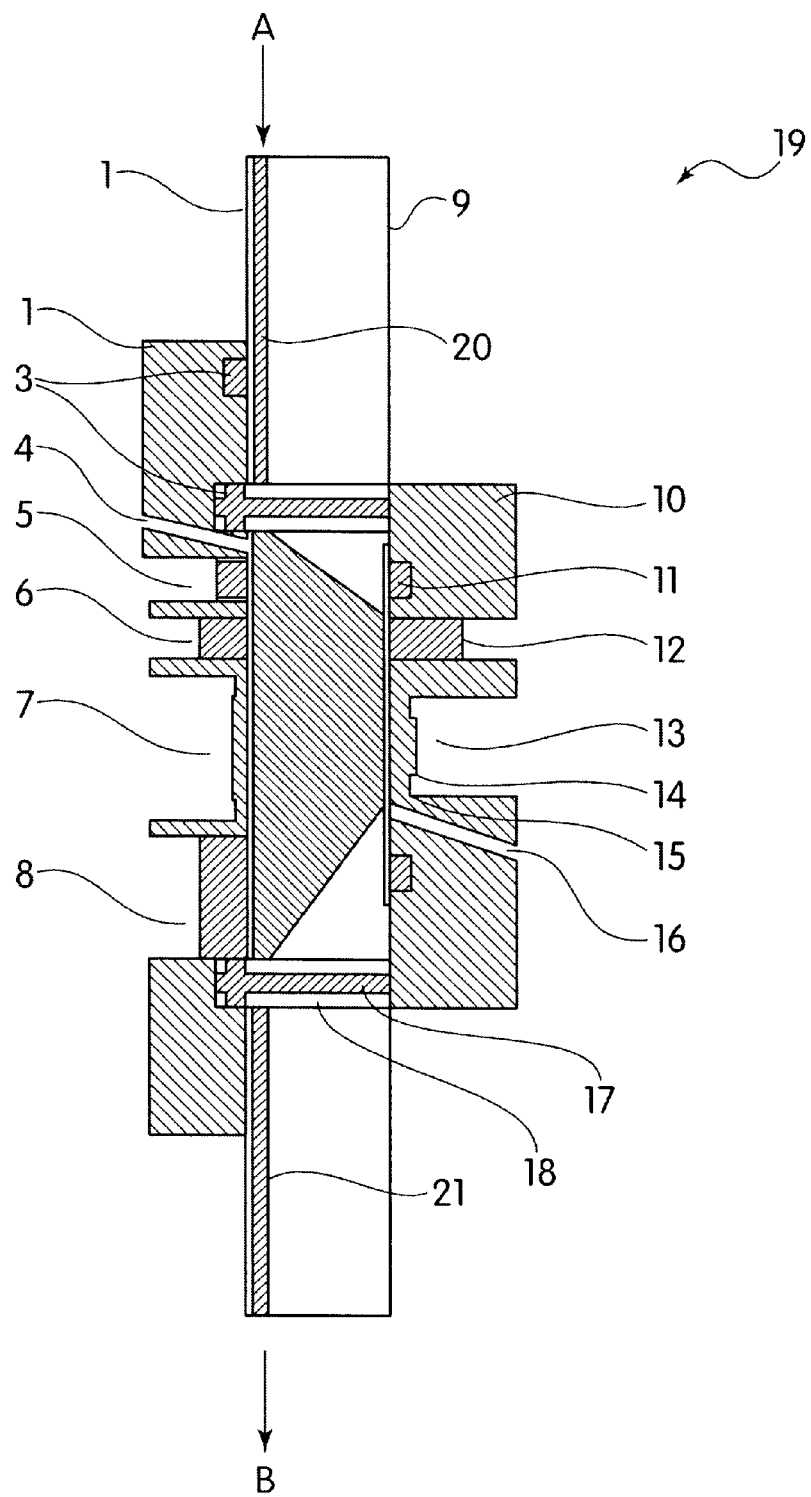
FIG. 1 shows a sectional view taken through the device according to one embodiment of the present invention.

A measurement chamber 15 having an inlet 20 and an outlet 21 is integrated into a disposable plastic unit 9, as shown in the drawing. The measurement chamber is sealed with films 1, 14 disposed on opposite sides of the measurement chamber. Measurement plates 2, 10, respectively having seals 3, 11 disposed on their outer edges, are provided on both sides of the measurement chamber and are in contact with the films 1, 14. The seals are inserted into corresponding grooves in the plates provided for this purpose, projecting slightly beyond the underside of the measurement plates. The two measurement plates are fastened to one another with, for example screws 17, and are separated by spacers 18.

Connections 4, 16 to provide a vacuum are disposed adjacent to the measurement plates. Suction is applied to films 1, 14 by the application of the vacuum, since seals 3, 11 prevent air from entering the space between the film and the underside of the measurement plates. In this manner, the sides of measurement chamber 15 are placed in close contact with the measurement plates disposed on both sides of the measurement chamber 15.

Several sensors can be mounted on the measurement plates. The measurement plates include through-holes or suitable recesses formed for this purpose. The sensors are inserted into the recesses and held in place, for example, by an adhesive. The underside of the sensors forms a seal flush with the underside of the measurement plate. Sensors that may be provided include, for example, a temperature sensor 5 and a pressure sensor 8, which measure the temperature and the pressure of the fluid in measurement chamber 15, adjacent to one side of measurement plate 2. Because of the close contact between the film and the underside of the sensor, both positive and negative pressures can be measured.

In one embodiment, an optical sensor and an ultrasonic sensor are also provided for transit measurements. The optical sensor can include, for example, a light source 12 and a light receiver 6, disposed so that they form a light barrier. The ultrasonic sensor similarly can include an ultrasonic transmitter 13 and an ultrasonic receiver 7.

Device 19 is preferably intended for use with a dialysis treatment machine. To that end, the device 19 is connected to the extracorporeal blood cycle of the dialysis machine, so that blood flows in the direction of arrows A, B.

Before performing the individual measurements, a vacuum is first applied to the connections 4, 16, so that films 1, 14 are placed in close contact with the sensors. Then, the sensors are activated by a control unit (not shown), so that the respective measurements can begin. Peltier elements, for example, may be used for temperature control of the measurement plates, to obtain a more accurate temperature measurement.

It will be apparent to those skilled in the art that various modifications and variations can be made in the structure and methodology of the present invention, without departing from the spirit or scope of the invention. Thus, it is intended that the present invention covers the modifications and variations of this invention provided they come within the scope of the appended claims and their equivalents.

What is claimed is:

1. A device for measuring selected parameters of a medical fluid, comprising:
   a measurement chamber through which the fluid flows, sealed on at least one side by a flexible membrane;
   a measurement plate having a peripheral seal on an outer edge, in contact with the flexible membrane;
   at least one sensor for measuring the selected parameters of the medical fluid, disposed on the measurement plate;
   a passage connecting an inlet opening between the measurement plate and the flexible membrane to a vacuum source, so that a vacuum can be established between the measurement plate and the flexible membrane;
   an additional measurement plate;
   at least one transmitter element mounted on a first one of the measurement plate and the additional plate; and
   at least one receiver element mounted on a second one of the measurement plate and the additional measurement plate, the receiver element paired with the transmitter element.

2. The device according to claim 1, wherein one of the at least one sensor is a pressure sensor for measuring a pressure on the flexible membrane, and another of the at least one sensor is a temperature sensor for measuring a temperature on the flexible membrane.

3. The device according to claim 1, wherein a contact area of the at least one sensor is in flush contact with a bottom edge of the measurement plate.

4. The device according to claim 1, further comprising:
   the additional measurement plate having a peripheral seal on an edge, disposed substantially parallel to the measurement plate;
   spacers disposed between the measurement plate and the additional measurement plate, for maintaining the two plates a selected distance apart;
   a second flexible membrane sealing a side of the measurement chamber facing the additional measurement plate, in contact with the additional measurement plate; and
   a second passage connecting a second inlet opening between the additional measurement plate and the second flexible membrane to the vacuum source, so that a vacuum can be established between the additional measurement plate and the second flexible membrane.

5. The device according to claim 4, further comprising an ultrasonic sensor mounted on the measurement plate for an ultrasound propagation time measurement.

6. The device according to claim 4, wherein the spacers engage centering holes provided in the measurement plate and additional measurement plate.

7. The device according to claim 1, wherein the transmitter element is an ultrasonic transmitter and the receiver element is an ultrasonic receiver.

8. The device according to claim 1, wherein the transmitter element is a light source, and the receiver element is a light receiver.

9. The device according to claim 1, wherein the peripheral seal is formed by a rubber ring inserted into a groove formed on the measurement plate, and projects beyond the outer edge of the measurement plate.

10. The device according to claim 1, wherein the flexible membrane is a thin plastic film.

11. The device according to claim 1, wherein the measurement chamber is a plastic chamber with rigid walls.

12. The decive according to claims 1, wherein the flexible membrane and the measurement chamber are integrated into a disposable part.

13. The device according to claim 1, wherein the measurement plate is a metal disk on which the at least one sensor is mounted.

14. The device according to claim 13, further comprising Peltier elements associated with the metal disk to keep the metal disk at a constant temperature.

15. The device according claim 1, further comprising a computer unit connected at the at least one sensor for processing signals from the at least one sensor.

16. A method for measuring selected parameters of a medical fluid, comprising:
   flowing the medical fluid through a measurement chamber having at least one side formed by a flexible membrane;
   forming a vacuum between the flexible membrane and at least one measuring plate, the at least one measuring plate being adjacent to the at least one side formed by the flexible membrane;
   measuring the selected parameters with sensors mounted on the at least one measuring plate, in contact with the flexible membrane;
   providing an additional measurement plate;
   providing at least one transmitter element mounted on a first one of the measurement plate and the additional measurement plate; and
   providing at least one receiver element mounted on a second one of the measurement plate and the additional measurement plate, the receiver element paired with the transmitter element. plates being maintained a selected distance apart by spacers.

17. The method according to claim 16, further comprising the steps of performing time propagation measurements using sensors mounted on two measurement plates disposed on opposite sides of the measurement chamber, the two measurement plates being maintained a selected distance apart by spacers.

18. The method according to claim 16, further comprising the step of maintaining the at least one measuring plate at a selected temperature.

* * * * *